United States Patent [19]

Schnabel et al.

[11] 4,394,290
[45] Jul. 19, 1983

[54] REGENERATION OF SUPPORTED CATALYSTS CONTAINING PALLADIUM AND/OR PLATINUM AND TELLURIUM

[75] Inventors: Rolf Schnabel, Schifferstadt; Hans-Martin Weitz, Bad Durkheim; Rolf Fischer, Heidelberg, all of Fed. Rep. of Germany

[73] Assignee: BASF Aktiengesellschaft, Ludwigshafen, Fed. Rep. of Germany

[21] Appl. No.: 335,503

[22] Filed: Dec. 29, 1981

[30] Foreign Application Priority Data

Jan. 23, 1981 [DE] Fed. Rep. of Germany ....... 3102087

[51] Int. Cl.³ .................. B01J 23/96; C07C 69/16; C07C 67/055
[52] U.S. Cl. .................. 252/412; 252/413; 252/414; 560/244

[58] Field of Search .............. 252/413, 415, 412, 420, 252/411 R, 414; 560/244

[56] References Cited

U.S. PATENT DOCUMENTS 4,092,267  5/1978  Fernholz et al. ............... 252/413
4,233,455 11/1980  Weitz et al. ................... 560/244

FOREIGN PATENT DOCUMENTS 2943407  5/1981  Fed. Rep. of Germany ...... 560/244
55-36427 3/1980  Japan ........................... 560/244
 834361  5/1960  United Kingdom ............. 252/413

Primary Examiner—P. E. Konopka
Attorney, Agent, or Firm—John H. Shurtleff

[57] ABSTRACT

A process for regenerating a supported catalyst for acyloxylations, which contains palladium and/or platinum and tellurium, with or without copper, wherein copper is applied to the catalyst to be regenerated.

10 Claims, 1 Drawing Figure

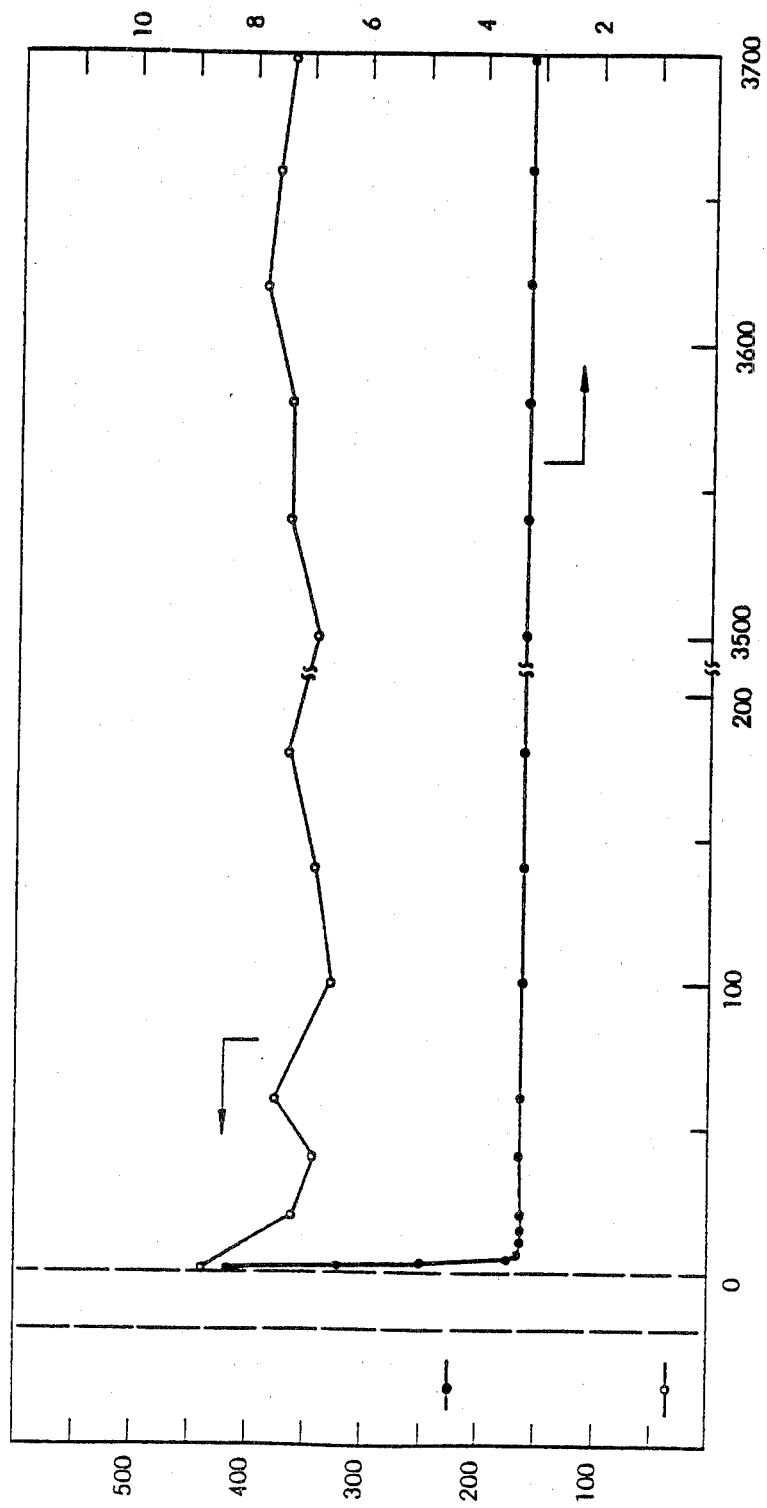

REGENERATION OF SUPPORTED CATALYSTS CONTAINING PALLADIUM AND/OR PLATINUM AND TELLURIUM

The present invention relates to a process for regenerating a supported catalyst which is used for acyloxylations and which contains palladium and/or platinum and tellurium.

Supported catalysts which contain palladium and/or platinum as well as tellurium, with or without copper, are examples of acyloxylation catalysts. They are used, for instance, to prepare butenediol esters by reacting a butadiene with a lower carboxylic acid and oxygen. Butenediol esters, eg. 1,4-diacetoxy-but-2-ene, are valuable intermediates, for example for the preparation of butene-1,4-diol, butane-1,4-diol and tetrahydrofuran. But-1-ene-3,4-diol diacetate (vinylglycol diacetate) can be used as an intermediate for the preparation of vitamins and other biologically active compounds, and 2-methyl-1,4-diacetoxy-but-2-ene and 1,1,4-triacetoxy-2-methyl-but-2-ene are valuable intermediates, for example for the synthesis of terpene compounds.

An important feature of a catalyst is its activity, ie. the amount of useful product obtained, under defined reaction conditions, per unit amount of catalyst per unit time. In the case of the continuous acetoxylation of butadiene, wherein butadiene is reacted with acetic acid and oxygen, the activity is expressed as the amount of butenediol diacetates, in g, produced per kg of catalyst per hour. A further important characteristic is the catalyst life, ie. the period over which the catalyst retains a sufficiently high activity. If the catalyst activity is plotted against the period of operation for which the catalyst has been used, a curve is obtained whose integral indicates the total amount of useful product obtained per unit amount of catalyst. This parameter, referred to as the productivity, can also be employed as a criterion of the quality of the catalyst employed. It is to be borne in mind that for industrial use, too short a life (at high catalyst activity) is just as unsatisfactory as too low a catalyst activity coupled with a very long life, even though in both these extreme cases the productivity per se is very good.

The above features of the catalyst are put in perspective by the expense in procuring the starting materials and in preparing the catalyst. For example an expensive catalyst must, to be as economical as a cheap catalyst, have a correspondingly higher productivity.

When using catalysts with high noble metal contents, reactivation or reprocessing of the catalysts is in general unavoidable, since the activity of any of these catalysts drops, after varying periods of operation, below an economically acceptable value.

A very economical method of regenerating or reprocessing the deactivated catalyst is therefore desirable. Thus, a variety of proposals for regenerating supported catalysts containing palladium and other metal components have been made. For example, Japanese Published Application No. 9,993 (1979) discloses that acetoxylation catalysts which contain palladium and tellurium on an active charcoal carrier can be reactivated by treating the catalysts of diminished activity with hydrogen at 300°–600° C. A similar effect is achieved if such a catalyst of diminished activity is first treated with hydrogen at 300°–600° C., then with oxygen at 150°–350° C. and lastly again with hydrogen at 300°–600° C. (Japanese Published Application No. 9,992 (1979)). Further, it has been disclosed that catalysts which contain palladium, rhodium, ruthenium or platinum on an active charcoal carrier, and which may additionally contain selenium and/or tellurium, can be reactivated by first treating them with a mineral acid, such as hydrofluoric acid, hydrochloric acid or nitric acid, and then reducing them at 200°–500° C. (Japanese Preliminary Published Application No. 39,283 (1978). Moreover, Japanese Patent Application No. 3,867 (1980) describes the regeneration of catalysts which contain palladium on an active charcoal carrier and which may additionally contain selenium, bismuth and/or tellurium, by treatment with acetic acid and oxygen.

It is true that the original catalyst activity can be restored by these methods. However, in continuous operation it is found that the catalysts reactivated in this way exhibit only relatively short lives, with relatively low activities, and accordingly low productivities. Further, it is a disadvantage that the active charcoal used as the carrier is attacked by oxidizing agents, such as oxygen or nitric acid, during reactivation of the catalyst. On the other hand, because of the high price of palladium it is necessary to remove the palladium from the catalyst carrier which, after a long reaction time, can no longer be reactivated, and to recover it. This again requires nitric acid, which oxidizes zero-valency palladium to divalent palladium, with evolution of nitric oxide. However, it is known that on treating active charcoal with nitric acid explosive detonation can occur, thus making safe working substantially more difficult.

We have found that a supported catalyst for acyloxylations, which contains palladium and/or platinum and tellurium, with or without copper, the copper content $A$ being from 0 to 2, where $A$ is the number of gram atoms of copper per gram atom of palladium and/or platinum, can be regenerated particularly advantageously by a method wherein sufficient copper is applied to the catalyst to be regenerated that the regenerated catalyst has a copper content $B=A+C$, where $A$ has the above meaning and $C$ is a number from 0.5 to 6, especially from 1 to 4.

The acyloxylation catalysts to be regenerated are described in, for example, German Pat. No. 2,217,452 and German Laid-Open Applications DOS No. 2,943,407 and DOS No. 2,820,519. Catalysts of the said type for example contain, based on catalyst weight, from 0.1 to 25% by weight of palladium or platinum, from 0.01 to 30% by weight of tellurium and from 0 to 30% by weight of copper. Preferred copper-containing catalysts are those which contain from 0.01 to 6, preferably from 1 to 3.5, gram atoms of copper and from 0.01 to 1, preferably from 0.01 to 0.4, gram atom of tellurium per gram atom of palladium or platinum and in which intermetallic phases of the composition $PdCu_3$, $PtCu_3$, $PdCu$ or $PtCu$ are detectable by X-ray diffraction.

In these catalysts the total amount of catalytically active metals applied to the carrier is, for example, from 0.01 to 30% by weight, based on the carrier. Examples of suitable carriers are active charcoal, bauxite, pumice, silica gel, kieselguhr or other forms of silica, magnesia, clay or alumina.

The catalysts mentioned are used for the preparation of butenediol esters by acyloxylating butadiene or substituted 1,3-dienes, eg. isoprene, 2,3-dimethyl-1,3-butadiene, 1,3-pentadienes, eg. piperylene, or acyloxy-substituted 1,3-butadienes, eg. 1-acetoxy-1,3-butadiene, 1-acetoxy-2-methyl-1,3-butadiene or 1-acetoxy-3-methyl-1,3-butadiene. The said diolefins are employed individually or as mixtures, which can also contain, for example, other hydrocarbons, such as monoolefins and paraffin hydrocarbons. Such mixtures are for example available as $C_4$-cuts. The acyloxylation is carried out in a conventional manner by treating the diene at 70°–180° C., in the gas phase or liquid phase, in the presence of the catalyst, with oxygen and a low molecular weight carboxylic acid, eg. formic acid, acetic acid or propionic acid. The reaction pressure depends on the process details and can be from atmospheric pressure to, for example, 100 bar. The acyloxylation is carried out batchwise or continuously, for example in a fixed bed, fluidized bed or three-phase moving bed.

The regeneration according to the invention can be carried out, for example, as follows: advantageously, the catalyst to be regenerated is treated with a solvent before applying copper in accordance with the invention. Examples of suitable solvents are the carboxylic acids with which the preceding acyloxylation has been carried out, and especially acetic acid. The catalyst to be regenerated is treated with the solvent, for example for half to 12 hours at from 20° to 200° C., using, for example, from 5 to 50 parts by weight of solvent per part by weight of catalyst. In place of the carboxylic acids, other solvents may be used, such as esters, eg. ethyl acetate, alcohols, eg. methanol or ethanol, hydrocarbons, eg. pentanes, hexanes, benzene and toluene. After this pretreatment, the catalyst is dried to remove solvent, for example in a stream of inert gas at from 50° to 200° C., under atmospheric or reduced pressure. To apply copper, the catalyst to be reactivated is, for example, then impregnated with a copper salt solution. The choice of the copper compound used (which can be monovalent or divalent) is not critical; for example, copper sulfate, copper chloride, copper nitrate, copper acetate or a copper-containing complex can be employed. It is also possible to start from metallic copper or a copper oxide or hydroxide, dissolve this in an acid and use the resulting copper salt solution. Examples of suitable solvents for copper salts are water, mineral acids, eg. hydrochloric acid and nitric acid, and, provided the solubility of the salt is not too low, organic solvents, eg. alcohols, ethers or carboxylic acid esters. If the catalyst to be regenerated is treated with a copper salt dissolved in an acid, such as nitric acid, a proportion of the metals may be dissolved off the carrier and pass into the copper salt solution. This is not objectionable, since all these metal salts are re-deposited on the carrier. Of course it is in principle also possible to dissolve off all the palladium and/or platinum, tellurium and/or copper from the carrier first, combine the resulting metal salt solution with the copper salt solution and re-deposit the salts, by stripping off the solvent, on the carrier, which may also be a fresh carrier or have been supplemented by addition of fresh carrier.

It is also possible to apply copper by vacuum metallization onto the catalyst to be regenerated.

The amount of copper to be applied is so chosen that the catalyst, after regeneration, contains from 0.5 to 6, especially from 2 to 4, gram equivalents of copper per gram atom of palladium and/or platinum or, where the catalyst to be regenerated already contains copper, that after regeneration the copper content is higher by from 0.5 to 6 gram atoms of copper per gram atom of palladium and/or platinum. It is also possible, but economically undesirable, to apply even larger amounts of copper. If the regeneration is being carried out with a catalyst which originally contained copper, it is advantageous to replace the amount of copper which has been dissolved off the catalyst during the preceding acyloxylation. It is also possible, simultaneously with the application of copper, to supplement the content of palladium, platinum and/or tellurium by addition of corresponding compounds, though in general only slight losses of these metals are observed. The carrier can also, where necessary, be supplemented. Palladium and/or platinum, tellurium and/or copper can be deposited on the carrier either simultaneously, or successively in optional sequence.

The resulting catalyst impregnated with metal salt solutions is then finished in a conventional manner. First, it is dried under atmospheric or reduced pressure, at from 50° to 200° C., to remove the solvents. Thereafter, the crude catalyst thus obtained is heated to a higher temperature in a stream of reducing gas. Any reduction process which converts the elements employed to the metallic state can be used. Examples of suitable reducing agents are hydrogen, methanol, hydrazine and formaldehyde. The salts can be reduced by, for example, a stream of hydrogen or nitrogen laden with a reducing compound, such as hydrazine, methanol or formaldehyde. The reduction of the dried catalyst can however also be carried out with a liquid reducing agent. The reduction temperature can be, for example, from 100° to 500° C., especially from 200° to 400° C. It is necessary that the metals should not be in the form of random physical mixtures, but that the palladium, platinum and copper in the catalyst should be in the form of an intermetallic palladium-copper or platinum-copper compound. This can be achieved, for example, by proceeding as described in German Laid-Open Application DOS No. 2,820,519, namely by heating the catalyst at 400°–900° C., preferably 500°–800° C. In general, there is a certain relation between the duration of heating and the temperature reached. For example, it has proved advantageous to heat the catalyst for from 15 minutes to 4 hours at from 400° to 900° C., a shorter heating time in general corresponding to a higher temperature. Since, in heating, a certain stabilization of the catalytically active state, once the latter is reached, is ultimately achieved, the time of heating is in general not subject to any particular maximum. If the carrier or metals tend to oxidize under the conditions of heating, the heating process is advantageously carried out in the presence of a reducing atmosphere, for example in pure hydrogen or in an inert gas, eg. nitrogen. In the catalyst thus treated, the presence of the intermetallic palladium-copper compound or platinum-copper compound can easily be ascertained by X-ray structural analysis.

Using the process according to the invention, the supported catalysts containing palladium and/or platinum and tellurium, with or without copper, are regenerated particularly effectively and durably, in a simple manner. One of the reasons why this advantageous result is surprising is that on renewed use of the regenerated catalyst for the acetoxylation of butadiene, the high activity of the catalyst remains preserved for a long time though a substantial part of the copper applied during regeneration is dissolved off again within only a short period of operation. This is shown particularly clearly by the diagram accompanying Example 4. It is also surprising that supported catalysts with an inorganic carrier, such as silica gel, give even more advantageous regeneration effects of the type described than do catalysts which contain active charcoal as the carrier.

Moreover, it must be described as very surprising that with catalysts which contain inorganic carriers, such as silica gel, even higher amounts of butenediol diacetate, and longer catalyst lives, are achieved after regeneration than can be achieved with the original catalysts.

EXAMPLE 1

(a) Use of a supported catalyst, containing Pd, Cu and Te, for the acetoxylation of butadiene:

5.2 kg of a catalyst which contains 4.6% by weight of Pd, 7.5% by weight of Cu and 0.4% by weight of Te on 4 mm active charcoal extrudates (2.73 gram atoms of copper per gram atom of palladium) are introduced into a reaction tube which has an internal diameter of 45 mm and height of 7 mm and can be heated. Per hour, 20 m$^3$ (S.T.P.) of nitrogen, 0.4–1 m$^3$ (S.T.P.) of oxygen, 10 liters of acetic acid and 1.5 liters of butadiene are passed through the catalyst bed from above, at 90 bar and 95° C., using the fixed bed/trickle method.

The reaction products from this and the subsequent Examples were examined by gas chromatography to establish their contents of the useful products trans-1,4-diacetoxy-but-2-ene (trans-1,4-BEDA), cis-1,4-diacetoxy-but-2-ene (cis-1,4-BEDA) and 3,4-diacetoxy-but-1-ene (3,4-BEDA). The abbreviation BEDA used subsequently refers to the sum of the above three isomeric diacetoxybutenes.

The activity at the start of the reaction is 290 g of BEDA/kg of catalyst . h. After the process has run for 820 h, the activity has fallen to 61 g of BEDA/kg of catalyst . h. At this stage, the metal content of the catalyst is 5.5% by weight of Pd, 2.4% by weight of Cu and 0.3% by weight of Te. Accordingly, this partially deactivated catalyst contains 0.73 gram atom of Cu per gram atom of Pd.

(b) Regeneration and re-use of the catalyst

The deactivated catalyst from Section (a) is impregnated with a solution of 400 g of Cu in 6.8 liters of 3 N nitric acid. The amount of solution used is just sufficient to ensure uniform wetting of the catalyst with liquid. After mixing the liquid phase and the solid phase for ½ hour, the liquid phase is evaporated off at 85°–90° C. under reduced pressure (from a waterpump), until no more condensate forms on the condenser. The catalyst is then introduced into a tube which can be heated, and is slowly raised to 150° C. in a stream of nitrogen under atmospheric pressure, and kept at this temperature until no more condensate and no more nitrous fumes are expelled. The stream of nitrogen is then saturated with methanol at room temperature and passed for 2 days, at a rate of 3 liters (S.T.P.)/cm$^2$ . h through the catalyst bed which is thermostatically kept at 250° C. or 400° C. Finally, the catalyst is heated to 800° C. and is kept at this temperature for ½ hour, during which hydrogen is passed through the catalyst bed at a rate of 3 l (S.T.P.)/cm$^2$. h. The catalyst is cooled to room temperature under a stream of inert gas, for example nitrogen.

The catalyst which has been regenerated in this way contains 4.6% by weight of Pd, 5.6% by weight of Cu and 0.6% by weight of Te, and accordingly contains 2.05 gram atoms of Cu per gram atom of Pd.

The regenerated catalyst is used as described in Section (a). Its initial activity is 440 g of BEDA/kg of catalyst . h. After the same operating time of 820 h, the activity is 62 g of BEDA/kg of catalyst . h.

EXAMPLE 2

(a) Use of a catalyst, containing Pd, Cu and Te, for the acetoxylation of butadiene:

800 g of a catalyst which contains 5.2% by weight of Pd, 8.3% by weight of Cu (ie. 2.7 gram atoms of copper per gram atom of Pd) and 0.5% by weight of Te on active charcoal (0.8–1.2 mm chips) is tested, using a fixed bed/bottom phase method, in a reaction tube which has an internal diameter of 45 mm and a height of 4 m, and can be heated. For this test, 25 liters (S.T.P.) of oxygen dissolved in 5 liters of acetic acid, and 1.25 liters of a C$_4$-cracking cut containing 25% of butadiene are pumped per hour, under a pressure of 75 bar at 95° C., through the catalyst bed from below. The initial activity is 410 g of BEDA/kg of catalyst . h and falls, after 400 h, to 274 g of BEDA/kg of catalyst . h. At that stage, the catalyst contains 4.9% by weight of Pd, 4.4% by weight of Cu and 0.5% by weight of Te. Accordingly, the partially deactivated catalyst contains 1.5 gram atoms of Cu per gram atom of Pd.

(b) Regeneration and re-use of the catalyst:

The catalyst, employed as described in Section (a) is impregnated with a solution of 41 g of Cu in 300 ml of 5 N nitric acid and regenerated as described in Example 1. After regeneration, it contains 5.0% by weight of Pd, 10.5% by weight of Cu and 0.6% by weight of Te, ie. 3.5 gram atoms of Cu per gram atom of Pd.

The regenerated catalyst is employed for acetoxylation by the method described in Section (a) of the present Example. Its initial activity is 525 g of BEDA/kg of catalyst . h. After the same operating time of 400 h, the activity is 275 g of BEDA/kg of catalyst . h.

EXAMPLE 3

(a) Use of a catalyst, containing Pd, Cu and Te, for the acetoxylation of butadiene:

3 g of the original catalyst of Example 2, in 30 ml of reaction medium, are stirred in an autoclave of 50 ml capacity under 20 bar at 95° C., using a magnetic stirring bar running at 150 rpm. Per hour, 3 liters (S.T.P.) of oxygen and 100 ml of a 10% strength by weight solution of butadiene in acetic acid are fed in and the corresponding amount of reaction medium is discharged.

The initial activity of the catalyst is 2,300 g of BEDA/kg of catalyst . h. After the experiment has run for 250 h, the activity has dropped to 370 g of BEDA/kg of catalyst . h and the Cu content in the catalyst has fallen by 60%. The deactivated catalyst contains 1.07 gram atoms of Cu per gram atom of Pd.

(b) Regeneration and re-use of the catalyst:

The regeneration is carried out similarly to Example 1(b), so as to increase the Cu content to 10% by weight (3.2 gram atoms of Cu per gram atom of Pd). On renewed use of the regenerated catalyst as described in Section (a), the activity is 2,600 g of BEDA/kg of catalyst . h initially, and 340 g of BEDA/kg of catalyst . h after 250 h.

EXAMPLE 4

(a) Use of a supported catalyst, containing Pd, Cu and Te, for the acetoxylation of butadiene:

4.3 kg of a catalyst which contains 4.7% by weight of Pd, 7.8% by weight of Cu (ie. 2.8 gram atoms of Cu per gram atom of Pd) and 0.5% by weight of Te on SiO$_2$ gel (1.2–3.0 mm chips) are used, by the method described in Example 1(a). The initial activity is 350 g of BEDA/kg of catalyst . h. After an operating time of 360 h, the activity has fallen to 10% of its initial value. The metal content of the deactivated catalyst is found to be 4.4% by weight of Pd, 4.5% by weight of Cu (1.7 gram atoms of Cu per gram atom of Pd) and 0.4% by weight of Te.

(b) Regeneration of the catalyst:

The deactivated catalyst is impregnated with a solution of 200 g of Cu in 4.6 liters of 3 N nitric acid and regenerated by the method described in Example 1(b). After this treatment, it contains 3.9% by weight of Pd, 8.4% by weight of Cu (=3.6 gram atoms per gram atom of Pd) and 0.4% by weight of Te. When the regenerated catalyst is used as described in Example 1(b), the initial activity is 440 g of BEDA/kg of catalyst . h, and after a further 3,700 h is still as high as 382 g of BEDA/kg of catalyst . h.

The diagram shows the activity of the catalyst (—o—o—) and the Cu content of the deactivated catalyst (—•—•—), as well as the catalyst activity and the Cu content (in % by weight) of the reactivated catalyst, as a function of the duration of the experiment (h=hours).

EXAMPLE 5

The catalyst, regenerated as described in Example 4, is used for acetoxylation in an autoclave as described in Example 3. Its initial activity is 3,330 g of BEDA/kg of catalyst . h, and after an operating time of 250 h the activity is still as high as 1,600 g of BEDA/kg of catalyst . h.

EXAMPLE 6

(a) Use of a supported catalyst, containing Pd, Cu and Te, for the acetoxylation of butadiene:

7.5 ml of a catalyst which contains 4.3% by weight of Pd, 9.0% by weight of Cu (ie. 3.5 gram atoms of copper per gram atom of Pd) and 1.0% by weight of Te on $SiO_2$ gel (0.8–1.0 mm chips) are introduced into a tube of 125 ml capacity. The tube, which is closed by a screen at the bottom, whilst at the top it merges conically into a tube of double the cross-section, is set up vertically in a 1.5 liter autoclave. Per hour, 4 liters (S.T.P.) of oxygen, 1 liter of acetic acid and 0.1 liter of butadiene are introduced, at 20 bar and 95° C., into the autoclave, and at the same time the corresponding amount of reaction medium is discharged. The reaction medium is passed upward through the tube, by means of a propellor, in such a way that the catalyst is distributed, in a fluidized state, over the volume of the tube of 125 ml capacity.

The activity is 3,330 g of BEDA/kg of catalyst . h initially, and 2,000 g of BEDA/kg of catalyst . h after an operating time of 260 h. After a total of 800 h, the activity has fallen to 30% of the initial value. At that stage, the catalyst contains 4.3% by weight of Pd, 2.8% by weight of Cu (1.1 gram atoms of Cu per gram atom of Pd) and 1.0% by weight of Te.

(b) Regeneration and re-use of the catalyst:

6.5 g of the partially deactivated catalyst are impregnated with a solution of 0.52 g of Cu in 7.5 ml of 3 N nitric acid and regenerated as described in Example 1(b). After this treatment, the metal contents are 4.0% by weight of Pd, 9.6% by weight of Cu (4.0 gram atoms of Cu per gram atom of Pd) and 1.0% by weight of Te. The initial activity of this catalyst, under the conditions mentioned in Section (a), is 5,150 g of BEDA/kg of catalyst . h. After 260 h, the activity is 3,080 g of BEDA/kg of catalyst . h.

EXAMPLE 7

(a) Use of a supported catalyst, containing Pd and Te, for the acetoxylation of butadiene:

3 g of a catalyst which contains 6.2% by weight of Pd and 1.1% by weight of Te on active charcoal are used as described in Example 3, Section (a). The catalyst has an activity of 1,600 g of BEDA/kg of catalyst . h initially, and 400 g of BEDA/kg of catalyst . h after an operating time of 250 h.

(b) Regeneration and re-use of the catalyst:

The regeneration is carried out similarly to Example 3(b), to give a catalyst containing 11.2% by weight of Cu (3.0 gram atoms of Cu per gram atom of Pd). On renewed use of the regenerated catalyst as described in Section (a), the activity is 5,000 g of BEDA/kg of catalyst . h initially and 1,930 g of BEDA/kg of catalyst . h after 250 h.

We claim:

1. A process for regenerating a supported catalyst for acyloxylations, which catalyst contains palladium or platinum or mixtures thereof as well as tellurium, with or without copper, the copper content A being from 0 to 2, where A is the number of gram atoms of copper per gram atom of the palladium or platinum or mixtures thereof, which process comprises:

impregnating the catalyst to be regenerated with a copper solution in such an amount that the regenerated catalyst has a copper content $B=A+C$, where A has the above meaning and C is a number from 0.5 to 6;

drying the impregnated catalyst at from 50° to 200° C.;

then treating the catalyst with a reducing agent at from 100° to 500° C.; and finally heating the catalyst at from 400° to 900° C.

2. A process as claimed in claim 1, wherein a supported catalyst which contains from 0.1 to 25 percent by weight of palladium or platinum, from 0.01 to 30 percent by weight of tellurium and from 0 to 30 percent by weight of copper is reactivated.

3. A process as claimed in claim 1, wherein a supported catalyst which contains from 0.01 to 2 gram atoms of copper and from 0.01 to 1 gram atom of tellurium per gram atom of palladium or platinum is reactivated.

4. A process as claimed in claim 1, wherein the supported catalyst to be reactivated contains active charcoal as the carrier.

5. A process as claimed in claim 1, wherein the supported catalyst to be reactivated contains silica gel as the carrier.

6. A process as claimed in claim 1, wherein the copper compound used to impregnate the catalyst is a monovalent or divalent copper salt or a copper-containing complex.

7. A process as claimed in claim 6, wherein the copper compound is a salt selected from the group consisting of copper sulfate, copper chloride, copper nitrate and copper acetate.

8. A process as claimed in claim 1 wherein the copper is dissolved in a solvent selected from the group consisting of water, mineral acids, and those organic solvents in which the solubility of the copper is not too low.

9. A process as claimed in claim 1, wherein the reducing agent is selected from the group consisting of hydrogen, hydrazine, methanol and formaldehyde.

10. A process as claimed in claim 1, wherein the final heating step at 400°–900° C. is carried out for a period of about 15 minutes to 4 hours.

* * * * *